US012806118B2

(12) United States Patent
Klewinghaus et al.

(10) Patent No.: US 12,806,118 B2
(45) Date of Patent: Nov. 24, 2026

(54) BAG HOLDER, SYSTEM, AND METHOD FOR EMPTYING AN EFFLUENT BAG

(71) Applicant: Fresenius Medical Care Deutschland GmbH, Bad Homburg (DE)

(72) Inventors: Juergen Klewinghaus, Oberursel (DE); Inge Knoblach, Offenbach am Main (DE); Robin Partenfelder, Oberursel (DE); Alexander Schroers, Frankfurt am Main (DE); Jan-Willem Walde, Linden (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 1238 days.

(21) Appl. No.: 17/774,008

(22) PCT Filed: Nov. 5, 2020

(86) PCT No.: PCT/EP2020/081111
§ 371 (c)(1),
(2) Date: May 3, 2022

(87) PCT Pub. No.: WO2021/089690
PCT Pub. Date: May 14, 2021

(65) Prior Publication Data

US 2022/0395430 A1 Dec. 15, 2022

(30) Foreign Application Priority Data

Nov. 6, 2019 (DE) ..................... 10 2019 129 933.0

(51) Int. Cl.
*A61J 1/16* (2023.01)
*A61B 50/13* (2016.01)
*A61J 1/10* (2006.01)

(52) U.S. Cl.
CPC ................. *A61J 1/16* (2013.01); *A61B 50/13* (2016.02); *A61J 1/10* (2013.01); *A61M 2209/084* (2013.01)

(58) Field of Classification Search
CPC ..... A61B 50/13; A61J 1/10; A61J 1/12; A61J 1/16; A61M 1/14; A61M 1/30;
(Continued)

(56) References Cited

U.S. PATENT DOCUMENTS 3,441,136 A * 4/1969 Serfass et al. .......... A61M 1/16 210/138
3,809,577 A * 5/1974 Thorsson et al. ....... A61L 11/00 4/144.1

(Continued)

FOREIGN PATENT DOCUMENTS

DE 2208804 1/1973
DE 102010011465 9/2011

(Continued)

OTHER PUBLICATIONS

International Search Report and Written Opinion in International Appln. No. PCT/EP2020/081111, mailed Apr. 6, 2021, 26 pages (with English translation).

*Primary Examiner* — Shefali D Patel
(74) *Attorney, Agent, or Firm* — Fish & Richardson P.C.

(57) ABSTRACT

The present disclosure relates to a bag holder for receiving a first effluent bag, which serves for receiving effluent resulting from a blood treatment being performed by a blood treatment apparatus and includes at least one closable effluent outlet opening and at least one effluent inlet opening. The bag holder includes one or several rollers and at least one of the following features: a holding device for holding the first effluent bag in the bag holder, a receptacle for receiving the first effluent bag or a section of the first effluent bag, a pump section for conveying the effluent out of the first effluent bag
(Continued)

being received in the bag holder, at least one effluent outlet line for guiding the effluent towards the pump section and/or out of the first effluent bag and/or at least one basin line for guiding the effluent into the first effluent bag and/or away from the bag holder.

13 Claims, 4 Drawing Sheets

(58) Field of Classification Search
CPC ........ A61M 1/34; A61M 1/3413; A61M 1/60; A61M 1/63; A61M 1/64; A61M 1/71; A61M 1/80; A61M 1/84; A61M 2209/08; A61M 2209/084

See application file for complete search history.

(56) References Cited

U.S. PATENT DOCUMENTS

| | | | | |
|---|---|---|---|---|
| 9,592,329 | B2 * | 3/2017 | Pohlmeier | A61M 1/1656 |
| 2005/0187529 | A1 * | 8/2005 | Reasoner | A61B 50/13<br>604/317 |
| 2011/0040242 | A1 * | 2/2011 | Fallon | B62B 3/02<br>280/47.35 |
| 2013/0062265 | A1 | 3/2013 | Balschat et al. | |
| 2020/0230301 | A1 | 7/2020 | Beisser et al. | |
| 2020/0306433 | A1 | 10/2020 | Heide et al. | |

FOREIGN PATENT DOCUMENTS

| | | |
|---|---|---|
| DE | 102015121065 | 6/2017 |
| DE | 102017122804 | 4/2019 |
| EP | 2130903 | 12/2009 |
| WO | WO 1995/020985 | 8/1995 |
| WO | WO 2014/066337 | 5/2014 |
| WO | WO 2019/016145 | 1/2019 |

* cited by examiner

BAG HOLDER, SYSTEM, AND METHOD FOR EMPTYING AN EFFLUENT BAG

CROSS-REFERENCE TO RELATED APPLICATIONS

The present application is the national stage entry of International Patent Application NO. PCT/EP2020/081111, filed on Nov. 5, 2020, and claims priority to Application No. DE 10 2019 129 933.0, filed in the Federal Republic of Germany on Nov. 6, 2019, the disclosures of which are expressly incorporated herein in its entirety by reference thereto.

TECHNICAL FIELD

The present disclosure relates to a bag holder as described herein and to a system as described herein. It further relates to a method for emptying an effluent bag.

BACKGROUND

Extracorporeal blood treatment is known in the prior art. In this, the patient's blood is withdrawn and led extracorporeally along a blood circuit and, for example, through a blood filter. The blood filter includes a blood chamber through which blood is led, and a dialysis liquid chamber, through which dialysis liquid is led. Both chambers are separated from each other by a semi-permeable membrane. Blood and dialysis liquid are mostly guided through the blood filter by the counter-current principle. The blood is purified in the blood filter. On exiting the blood filter, the dialysis liquid, from now on referred to as dialysate, is regarded as used and is discarded. In addition to the dialysate, the fluid to be discarded also includes filtrate, which includes water which has been withdrawn from the blood in the blood filter. Filtrate and dialysate will be referred to individually or collectively in the following simply as effluent.

In the prior art, the effluent is, directly discarded via an effluent outlet line or above all, in the case of an acute treatment, it is led to an effluent bag and is first stored there. After completion of the blood treatment, or in bag emptying intervals taking place during the blood treatment (intervals in which the effluent bag is emptied), the effluent is discarded from the effluent bag into, e.g., a sink or into a differently designed basin.

An aspect of the present disclosure is to specify a bag holder and a system with a bag holder as described herein.

Further, a method for emptying the effluent bag is specified and is executable with the above-mentioned system.

The aspect according to the present disclosure is achieved by a bag holder as described herein and by a system as described herein. In addition, it is achieved by a method as described herein.

SUMMARY

All the advantages achievable with the method described herein may in certain embodiments be achieved undiminished by the apparatuses as described herein and vice versa.

The present disclosure relates to a bag holder. It serves for receiving a first effluent bag. The effluent bag serves for receiving the effluent which is produced during a blood treatment executed by a blood treatment apparatus and which is initially collected in a second effluent bag. The first effluent bag includes at least one closable effluent outlet opening (or first connection of the interior of the first effluent bag to an exterior of the first effluent bag) and a preferably likewise closable effluent inlet opening (or second connection of the interior of the first effluent bag to its exterior).

The bag holder includes one roller or several rollers, or one wheel or several wheels, for rolling the bag holder. It also optionally includes at least one of the following features in any combination:

- a holding device, for example with one or more hooks, for example four, to engage in optional eyelets of the effluent bag to be held. The optional holding device is provided for holding the first effluent bag at or in the bag holder. It can optionally be designed to hold the first effluent bag in a hanging manner. The latter may offer the advantage that the effluent present in the first effluent bag can converge in or near its bottom region. There, it may be centrally removed from the first effluent bag by only one access to the bag interior (the effluent outlet opening);
- an, optionally channel-shaped, receptacle, which is suitable for receiving the first effluent bag or a section thereof. The receptacle may be designed, e.g., by the configuration of its optional channel shape, to hold the first effluent bag in a position in which the effluent present in the first effluent bag converges in its bottom region or near it and being collected there it may be removed from the first effluent bag by only one access (the effluent outlet opening) to the bag interior;
- a pump section for conveying effluent out of and/or into the first effluent bag received in or on the bag holder;
- at least one effluent outlet line for guiding effluent to the pump section and/or out of the first effluent bag; and/or
- at least one basin line for guiding effluent into the first effluent bag and/or away from the bag holder.

The system described herein for treating a patient's blood, e.g., by dialysis and/or filtration, includes at least one blood treatment apparatus and at least one bag holder as described herein. Here, the bag holder includes one or several first effluent bags, and the blood treatment apparatus includes one or several second effluent bags, wherein the blood treatment apparatus is connected in fluid communication with the at least one second effluent bag in order to temporarily store effluent therein during the blood treatment.

The method described herein for emptying an effluent bag, which has been at least partially filled with effluent during a treatment of a patient's blood, includes at least the following:

a. providing a system as described herein
b. connecting the effluent outlet opening of the second effluent bag to the effluent outlet line of the bag holder such that a fluid communication is established between the interior of the second effluent bag and the interior of the effluent outlet line for guiding effluent out of the second effluent bag; and
c. conveying effluent, wherein this is sucked out of the second effluent bag by the pump section and the effluent outlet line and pumped along the basin line into the first effluent bag of the bag holder.

Embodiments may include some, several or all of the features mentioned below in any combination unless the person skilled in the art recognizes the specific combination as technically impossible.

In all of the aforementioned or following statements, the use of the expression "may be" or "may have" and so on, is to be understood synonymously with "preferably is" or "preferably has," and so on, respectively, and is intended to illustrate embodiments according to the present invention.

Whenever numerical words are mentioned herein, the person skilled in the art shall recognize or understand them as indication of a numerical lower limit. Unless it leads the person skilled in the art to an evident contradiction, the person skilled in the art shall comprehend the specification for example of “one” as encompassing “at least one”. This understanding is also equally encompassed by the present invention as the interpretation that a numerical word, for example, “one” may alternatively mean “exactly one”, wherever this is evidently technically possible for the person skilled in the art. Both are encompassed by the present invention and apply to all numerical words used herein.

Whenever an embodiment is mentioned herein, it is then an exemplary embodiment.

In some embodiments, the pump section of the bag holder is a disposable product.

In several embodiments, the pump section includes an impeller or a pump rotor.

In some embodiments, the effluent outlet line and/or the basin line are in fluid or conveyance communication with the pump section, and in particular with couplings of the pump section for hose lines.

In several embodiments, the pump section, or a section thereof, such as a pump head, is releasably latched to another section of the bag holder, for example to its main body. Releasable latching devices may include clamp, clip and/or hook/eyelets connections.

In some embodiments, the pump section is connected to a pump drive, which can optionally be detached therefrom, or is prepared to be connected to such a pump drive.

In several embodiments, the pump section or pump drive includes a rechargeable voltage source, e.g., a rechargeable battery or accumulator, or is connected thereto.

In some embodiments, the first effluent bag of the bag holder has an effluent inlet opening and an effluent outlet opening, wherein the effluent inlet opening can be arranged higher than the effluent outlet opening.

In several embodiments, the pump section, an optional impeller thereof and/or at least one of its couplings for connecting the pump section to the effluent outlet line or to the basin line are arranged below the effluent outlet opening of the second effluent bag.

In some embodiments, the bag holder has a handle for pushing or pulling the bag holder. The handle can be arranged at a suitable height so that the bag holder can be pulled or pushed by a person in an upright position.

In several embodiments, at least one of the rollers or one of the wheels of the bag holder includes an activatable braking device or brake mechanism. An activation mechanism may be provided on one or more of the wheels or rollers and/or may be actuated by foot or by hand. For example, an activation element for locking and/or releasing the braking device can be provided on the handle.

In some embodiments, the bag holder includes a pump section for pumping the effluent out of the first effluent bag into the drain. The blood treatment apparatus or another, e.g., mobile, device does not have such a pump section in these embodiments.

In several embodiments, the receptacle is bowl-shaped or channel-shaped and includes a through-opening for an access for the effluent outlet line to the effluent outlet opening, and can be equipped with a third connector for the connection to the effluent outlet line.

In some embodiments, the pump section includes a disposable impeller pump. After use, the first effluent bag including the pump section can be disposed of or cleaned by rinsing with disinfectant.

The effluent outlet line optionally includes a length between 10 cm and 50 cm, e.g., between 16 cm and 28 cm, about 26 cm, and/or an inner diameter between 8 mm and 15 mm, such as 11 mm.

The basin line optionally includes a length between 50 cm and 7 m, e.g., between 50 cm and 150 cm, between 50 cm and 100 cm, and/or an inner diameter between 8 mm and 25 mm, e.g., 10 mm to 15 mm or 11 mm to 12 mm.

In some embodiments, the effluent outlet line and/or the basin line are flexible hose lines.

In several embodiments, the first and/or the second effluent bag are flexible, thin-walled bags, for example made of or including film, which can advantageously save disposal costs.

In some embodiments, the first and/or the second effluent bag are rigid containers suitable for the subsequent rinsing and reuse thereof.

The position of the effluent outlet opening of the second effluent bag at the treatment apparatus may be, by way of example, 23 cm or 28 cm above the floor or any value in between. An example of a filling height of 28 cm should be given here.

In several embodiments, the basin, e.g., a wall system for media supply and disposal, is configured with a free-fall section for the effluent discarded into it, which can be important for the ventilation, as described below in stating the advantages. The provision of a drop height further advantageously prevents fluid from being sucked back into the line if negative pressure or vacuum is created in the line. This may in turn be of benefit to hygiene.

In some embodiments of the system described herein, the blood treatment apparatus is configured as a hemodialysis apparatus, hemofiltration apparatus or hemodiafiltration apparatus, e.g., as an apparatus for the acute, the chronic or the continuous renal replacement therapy (CRRT).

In several embodiments of the system described herein, the second effluent bag includes an effluent outlet opening, e.g., with a first connector of a first type for connecting an effluent outlet line.

Thereby, the effluent outlet line is connected at one of its ends to a first coupling of the pump section, wherein its other end includes a second connector of the first type which can be used for connection to the first connector of the first type. The first coupling of the pump section is located at its liquid inlet or fluid inlet.

In addition, in such an embodiment, the effluent outlet opening of the first effluent bag can include a third connector of the first type for connection to the second connector of the first type.

The first connector and the third connector may include the same diameter, e.g., a diameter of 11 mm.

In some embodiments of the system described herein, the basin line is connected at one of its ends to a second coupling of the pump section. The second coupling of the pump section is located at its liquid outlet or fluid outlet.

Hereby, the other end of the basin line includes a fourth connector of a second type.

Herein, the second type may be identical to the first type. The second type may herein alternatively differ from the first type, e.g., by its diameter, type of connection (connector, thread, etc.), and/or in another way.

In such an embodiment, the system can further include a basin with an optional fifth connector of the second type for connection to the fourth connector of the second type.

As an example of the position of the basin or the fifth connector, a flexible height between 0 cm and 150 cm may be specified, e.g., 10 cm to 120 cm or 25 cm to 100 cm. In some embodiments, the fifth connector is configured to be connected to the fourth connector of the basin line.

In some embodiments of the system, the effluent inlet opening of the first effluent bag includes a sixth connector of the second type for connection to the fourth connector of the second type.

In some embodiments of the method described herein, the effluent outlet line is connected to the effluent outlet opening of the first effluent bag via the third connector of the first type at the second connector of the first type in order to discharge effluent from the first effluent bag into the basin.

Hereby, the fourth connector of the basin line is arranged above or in the basin. The effluent is conveyed out of the first effluent bag of the bag holder, whereby it is sucked using the pump section out of the first effluent bag of the bag holder along the effluent outlet line and pumped along the basin line into or over the basin.

In some embodiments of the method, the fourth connector of the second type is connected to the fifth connector of the second type. This may serve to fix the basin line in or at the basin and thus advantageously prevent an undesired dripping, spilling or overflowing of effluent.

The first and/or second type of connector may be a quick coupling connector, e.g., a so-called Walther coupling (Fa. Walther-Prazision, Carl Kurt Walther GmbH & Co. KG, Haan, Germany). The connectors may, for example, be designed to be cylindrically flexible for pushing or sliding. Optionally, they may also simply be a connection for pushing a pipe, for example for pushing the basin line onto a drain bell.

In some embodiments, the pump section, an optional impeller thereof and or at least one of its couplings for connecting the pump section to the effluent outlet line or to the basin line is arranged below the effluent outlet opening of the second effluent bag.

In some embodiments of the method, the bag holder is moved towards the basin, using the rollers or wheels, in order to empty effluent out of the first effluent bag and into the basin.

In some embodiments, the first effluent bag of the bag holder has a larger capacity than the second effluent bag of the blood treatment apparatus, which usually has a capacity of e.g., 10 l. The capacity of the first effluent bag can be several times the capacity of the second effluent bag, in particular six to nine times. This has the advantage that several contents of the one second effluent bag, or the contents of several second effluent bags, e.g., of different blood treatment apparatuses of the same infirmary of the hospital or clinic, may be emptied into the first effluent bag before the first effluent bag has to be emptied.

Suitable, optional holders may be provided at the bag holder. They can make it easier to hold, e.g., the free ends or other sections of the effluent outlet line and/or the basin line on or at the bag holder.

In some embodiments, the pump section is magnetically mounted and/or driven and includes, e.g., the pump head. This pump head is designed, for example, as an impeller pump head or as its rotor. This type of drive serves for protecting the patient against an electric shock when emptying the second effluent bag.

In several embodiments, the pump drive is manually connected to the pump section that includes the pump head.

In some embodiments, the pump drive is optionally equipped with a magnetic section, e.g., designed as coils with an iron core. This is used for magnetic coupling and/or magnetic driving of components, e.g., of a magnetically driven pump rotor of the pump section. The drive can be contactless.

In several embodiments, the system or the bag holder encompasses an induction charging station for charging the rechargeable battery of the pump drive. The induction charging station has optional control electronics, which is configured to detect the placing of the pump drive on the induction charging station and to charge the battery.

The induction charging station may be, or may include, a platform or a base plane for the pump drive.

The present disclosure relates to a bag holder which optionally includes at least one pump section with a pump rotor. The pump section may be provided to be functionally connected to or brought together with a pump drive. The pump section, and optionally also all other sections of the bag holder, have in some embodiments no device(s) for connecting the pump section to the pump drive, except for an optional magnetic connection and/or use of gravity, e.g., no devices for jamming, latching, locking, and/or similar.

In some embodiments, the pump drive includes an induction charging coil for charging the voltage source or the rechargeable battery.

In several embodiments, the housing of the pump drive includes a pump drive base section for placing the pump drive on a pump drive base surface.

In some embodiments, the housing of the pump drive includes a connecting section for, e.g., functionally, connecting the pump drive to the pump section containing a pump rotor. The connecting section may hereby be a cavity, one or several openings, one or several blind openings or the like.

In several embodiments, the pump drive-base section and the connecting section lie at opposite ends of the housing of the pump drive or are associated therewith.

In some embodiments, the pump drive includes at least one, e.g., colored, lighting device. This may be designed as a ring, e.g., as an LED or LED color ring.

The lighting device may be positioned, e.g., in or at the housing of the pump drive.

In several embodiments, the control electronics of the pump drive is configured with, or connected to, a wireless module.

In some embodiments, the control electronics is configured with, or connected to, at least one motion sensor.

In some embodiments, the control electronics is configured to switch off the lighting device when or after the complete charging of the voltage source or of the rechargeable battery is achieved.

In several embodiments, the electrical rating is between 25 and 40 watts (W), e.g., between 30 and 35 W or 32 W.

In several embodiments, the drive voltage of the electric drive of the pump is 24 V.

In some embodiments, the pump section includes a device for releasably fastening said pump section to a section of the bag holder.

In several embodiments, the device for releasably fixing the pump section is, or includes, a clamp device or a latching or clip device.

In several embodiments, the pump drive, the pump section and/or another component of the pump includes in any case no mechanical connecting device for connecting the pump drive to the pump section, except for the base surface of the pump section on which the pump drive is placed in order to obtain the functioning pump.

An advantage achievable therewith may be that the pump drive can simply be pulled upwards or lifted off at any time (even during the pumping process). In particular, this may be done with one hand, e.g., when no mechanical connecting devices have to be opened beforehand, since these devices are not provided in theses embodiments.

The magnetic section of the pump rotor may be a permanent magnet.

In some embodiments, the storage capacity of the rechargeable battery of the pump drive is between 800 mAh and 1800 mAh, between 1000 mAh and 1500 mAh, or approximately or exactly 1100 mAh.

In several embodiments, the effluent outlet line includes at least one check valve, e.g., upstream of the pump drive. When the effluent bag is uncoupled, the check valve can prevent an unintentional escape of effluent from the effluent outlet line, which is good for or which is a benefit for cleanliness and hygiene.

In several embodiments, the pump section or the pump, having the design for example as an impeller pump, is configured in such a way that it can empty the effluent bag filled with ten liters of effluent, at least with a maximum adjustable flow, in about five minutes or less, e.g., in about one minute.

In several embodiments, the bag holder or system does not have two trolleys that can be separated from each other and/or nested inside each other.

In some embodiments, the bag holder includes no filter element, e.g., no HEPA (High Efficiency Particulate Air) filter, and/or no filter element in its effluent outlet line and/or in its basin line.

In several embodiments, the system has no fluid connection between a dialysate outlet line of the blood treatment apparatus (with which effluent is guided from the blood filter (see reference numerals 102 and 303 of FIG. 1) into the second effluent bag of the blood treatment apparatus) and the first effluent bag. According to the present disclosure, the dialysate outlet line is not connected to an effluent inlet line of the first effluent bag. Accordingly, suitable or certain couplings may not be provided for this purpose.

In several embodiments, the first effluent bag of the bag holder includes two openings which can be positioned at least 20 cm, 25 cm, 30 cm or 35 cm apart.

The two openings can be located in an upper area (e.g., upper third of the height) of the first effluent bag or in a lower area (lower third of the height) of this effluent bag.

In some embodiments, the bag holder is not designed to be insertable (at least partially) into a frame or housing of the blood treatment apparatus and/or has no connection devices for its connection to the blood treatment apparatus, in any case not beyond its temporary fluid connection to the second effluent bag.

In several embodiments, the system has only exactly one bag holder.

In several embodiments, the first effluent bag is detachably received in or on the bag holder.

In several embodiments, the bag holder includes only one frame and/or only one sliding unit/frame rolling on its own.

In some embodiments, the bag holder has only four rollers or wheels for moving it.

In several embodiments, the pump section, which may serve as a vacuum source, is part of the bag holder and therefore movable, e.g., rollable, together with the other elements of the bag holder. The pump section is optionally not arranged to be removable from the first effluent bag or its receptacle at the bag holder in a rolling manner.

In some embodiments, the bag holder has no further electrical consumers other than the pump section or elements of the pump connected thereto.

In several embodiments, the basin is a component of the system which has no rollers for rolling it in the room.

In some embodiments, the basin does not include a pump.

In several embodiments, the bag holder does not include three-way taps or three-way valves.

In some embodiments, the system or the bag holder includes, for the purpose of being connected to the first or to the second effluent bag, to sections of the basin and/or to sections of the blood treatment apparatus, no solid or rigid plug connections, at least none that are not themselves connected to a hose or to a part of an effluent bag.

In several embodiments, the basin is a final destination for the effluent, preferably at least as far as the range of influence by the medical staff extends or reaches.

In some embodiments, the basin has only one connection/port/connector/coupling which is required in or by the system described herein or is used in the method described herein.

In some embodiments, the basin is not mobile, e.g., does not include rollers.

In several embodiments, the bag holder and/or its pump section does not include a valve nor a bypass, and, moreover, in some embodiments it does not include a switch for reversing a conveying direction.

In some embodiments, the bag holder is not a blood treatment apparatus, includes no pump for fresh dialysis liquid, no source of fresh dialysis liquid, no blood pump and/or no blood filter or holder or connections for it.

In several embodiments, the rollers of the bag holder do not, even partially, support the weight of a blood treatment apparatus, a pump for fresh dialysis liquid, a source of fresh dialysis liquid, a blood pump and/or a blood filter or holder or connections for them.

Some or all of the embodiments may include one, several or all of the aforementioned and/or the following stated advantages.

One advantage of the bag holder may be that the second effluent bag which was filled by the blood treatment apparatus no longer has to be carried nor even lifted to a basin, e.g., a sink, a toilet, a gully, etc., by the hospital staff due to the emptying thereof into the first effluent bag arranged on the bag holder. Since full effluent bags usually weigh around 10 kg, the hospital staff is considerably relieved from this work if the mobile, separately usable bag holder, for example, is placed directly next to the blood treatment apparatus, and the heavy, second effluent bag, which is to be emptied has no longer to be laboriously carried around or repositioned.

Providing the first effluent bag of the bag holder as a pendulum or transport bag allows the effluent to be discarded at a sufficient distance from places where hygiene may be critical, e.g., a sink, a toilet or a basin. Advantageously, hygiene problems (which in the worst case could lead to re-contamination) may thus be avoided, unlike with conventional methods.

Another advantage of the bag holder may also be the maximum flexibility with regard to the spatial conditions, for example in treatment rooms or in intensive care units (ICU).

Since the second and fourth connectors discussed above (hereinafter referred to as K2 or K4) may always find a fixed place at one of the other connectors or at optional holders, it is advantageously ensured that the effluent outlet line and the basin line do not hang down and also that nothing drips when the bag holder is driven away.

If the capacity of the first effluent bag is optionally larger (measured by the capacity of the second effluent bag), several second effluent bags or effluent bag contents may be emptied into the first effluent bag before the first effluent bag has to be emptied. This may save time and money.

Advantageously, the pump section may only require about one minute for emptying the second effluent bag with a capacity of 10 l (into the first effluent bag). This is less time than any pending activity takes which is to be performed at the blood treatment apparatus, e.g., such as equipping it with fresh solution bags. These activities can therefore be carried out simultaneously to the emptying of the second effluent bag, which in turn may save time.

When an impeller pump is used, the height of the pump section relative to the effluent outlet opening of the second effluent bag on the blood treatment apparatus and to the effluent outlet opening of the first effluent bag on or in the bag holder can advantageously serve to enable the venting of a previously air-filled pump section.

Another possible advantage to be mentioned is that when arranging the end of the basin line with the fourth connector, which lies opposite to the end with the second coupling of the pump section, above the possible filling level of the first effluent bag on the bag holder, a return of the liquid within the basin line may be made possible in case of a halt of the pump without liquid draining out of the first effluent bag. The backflow of effluent displaces the air that is usually sucked in towards the end of an emptying process in the pump section, in particular when using an impeller pump, and displaces said air in the direction of the second effluent bag. For this purpose, at least the first coupling of the pump section may be arranged at a distance less than 27 cm, e.g., less than 22 cm, below the effluent outlet opening of the second effluent bag, in order to ensure a reliable ventilation. Due to the ventilation, the pump section may be prepared for its following conveying activity.

Advantageously, the bag holder also avoids the risk of electrical contact between the effluent and the ground when discharging the content of the effluent bag, which would exceed the allowable patient leakage currents, since the bag holder itself does not need to be connected to a power supply. Using a pump driven by a rechargeable battery, will not expose the patient to an electrical accident or shock or voltage damage.

Another advantage of the bag holder may be that it can be used to optimize operations at the blood treatment apparatus. Since the emptying of the full, first effluent bag takes place only comparatively late depending on its size, the first effluent bag "parked" on the bag holder may, for example, only then be pumped empty as soon as the workflows for the patient allow it.

BRIEF DESCRIPTION OF THE FIGURES

In the following, the present invention is purely exemplarily described with reference to the accompanying drawings. In the drawings, identical reference numerals refer to the same or to identical components. In the figures, the following applies.

DETAILED DESCRIPTION

Figure 1:
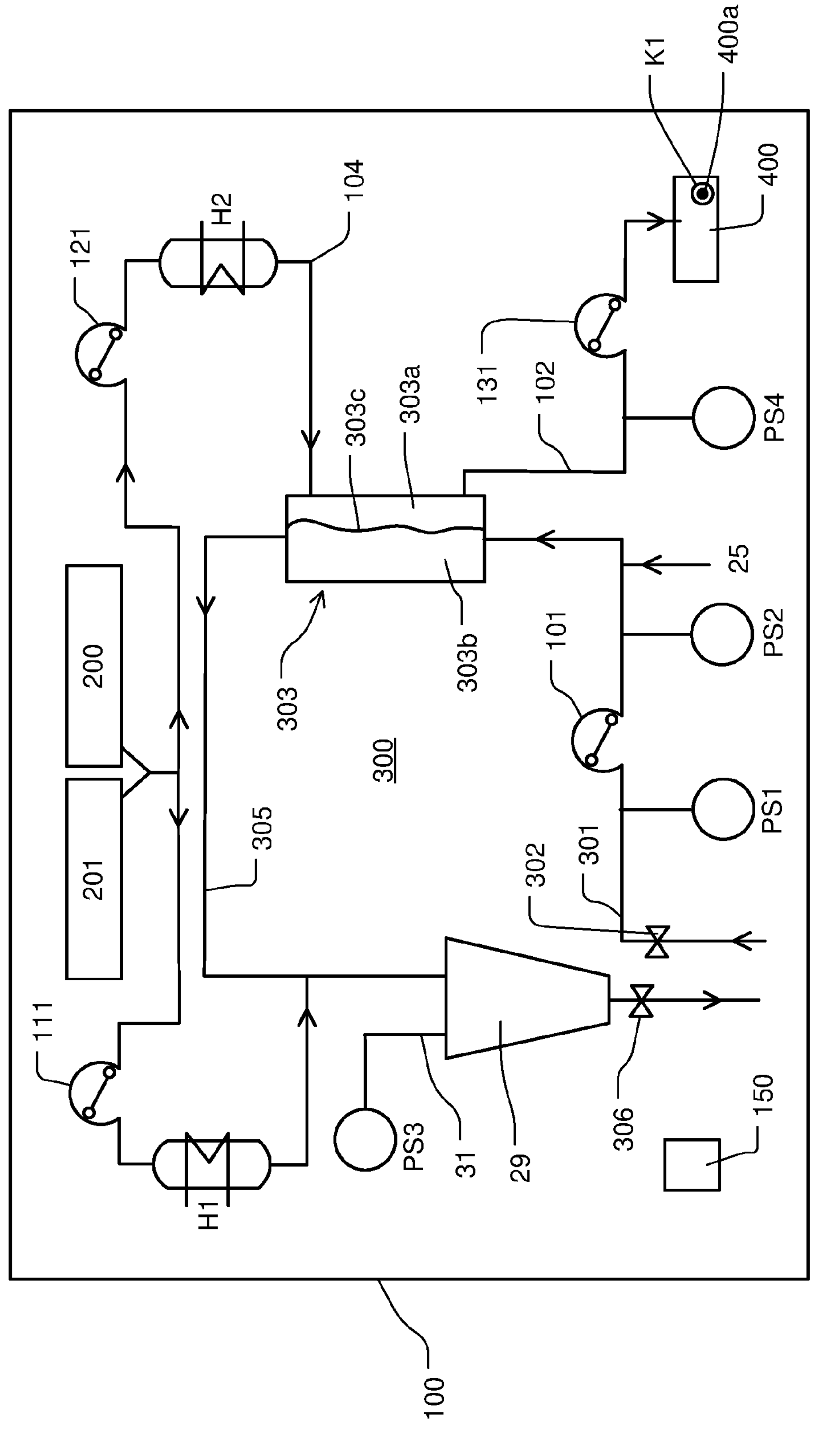
FIG. 1 shows a highly simplified illustration of a flow diagram of a blood treatment apparatus having an extracorporeal blood circuit.

FIG. 1 shows a highly simplified illustration of a process flow diagram of a blood treatment apparatus 100 of a system, optionally connected to an extracorporeal blood circuit 300 and a discharge hose system for an effluent bag 400, being herein designated as a second effluent bag. The extracorporeal blood circuit 300 includes a first line 301, here an arterial line section.

The first line 301 is in fluid communication with a blood treatment apparatus, here exemplarily a blood filter or dialyzer 303. The blood filter 303 includes a dialysis fluid chamber 303*a* and a blood chamber 303*b*, which are separated from each other by a mostly semi-permeable membrane 303*c*.

The extracorporeal blood circuit 300 further includes at least a second line 305, here a venous line section. Both the first line 301 as well as the second line 305 may serve as their connection to the vascular system patient (not shown).

The first line 301 is optionally connected to a (first) hose clamp 302 for blocking or closing the line 301. The second line 305 is optionally connected with a (second) hose clamp 306 for blocking or closing line 305.

The blood treatment apparatus 100 which is represented, only by some of its devices and merely schematically, in FIG. 1, includes a blood pump 101. During the patient's treatment, the blood pump 101 conveys blood through sections of the extracorporeal blood circuit 300 towards the blood filter or dialyzer 303. This is illustrated by the small arrow tips, which are used in each of the figures to generally indicate the direction of flow.

Fresh dialysis liquid is pumped from a source 200 along the dialysis liquid inlet line 104 into the dialysis liquid chamber 303*a* by a pump for dialysis liquid 121, which may be designed as a roller pump or as an otherwise occluding pump. The dialysis liquid leaves the dialysis liquid chamber 303*a* in the direction of the second effluent bag 400 as dialysate possibly enriched by filtrate, and is herein referred to as effluent.

The source 200 may be, for example a bag or a container. The source 200 may also be a fluid line through which online and/or continuously generated or mixed liquid is provided, for example a hydraulic output or—connection of the blood treatment apparatus 100.

A further source 201 with substituate may be optionally provided. It may correspond to the source 200 or be a separate source.

An only outlined control device or closed-loop control device 150 may be configured for the closed-loop controlling or the controlling of the blood treatment apparatus.

There is indicated in FIG. 1 on the bottom right where a second effluent bag 400 may be connected to the blood treatment apparatus 100. The second effluent bag 400 includes an effluent outlet opening 400*a* and a first connector K1.

In addition to the aforementioned blood pump 101, the arrangement in FIG. 1 further includes purely optionally a series of further pumps, in each case optional, namely the pump 111 for substituate, the pump 121 for dialysis liquid and the pump 131 for the effluent.

The pump 121 is provided to supply the blood filter 303 with dialysis liquid from a source 200, for example a bag, using a dialysis liquid inlet line 104, and via an optional existing bag heating H2 with a heating bag.

The thus supplied dialysis liquid exits again from the blood filter 303 via a dialysate outlet line 102 supported by the optional pump 131, and may be discarded.

Upstream of the blood pump 101, an optional arterial sensor PS1 is provided. During a patient's treatment it measures the pressure in the arterial line.

Downstream of the blood pump 101, but upstream of the blood filter 303 and if provided, downstream of an addition site 25 for heparin, a further optional pressure sensor PS2 is provided. It measures the pressure upstream of the blood filter 303 ("pre-hemofilter").

Again, a further pressure sensor for measuring the filtrate pressure of the blood filter 303 may be provided as PS4 downstream of the blood filter 303 or upstream of the pump 131 in the dialysate outlet line 102.

Blood, which leaves the blood filter 303, passes through an optional venous blood chamber 29, which may include a ventilation device 31 and/or a further pressure sensor PS3.

The control device or closed-loop control device 150 shown in FIG. 1 may be in cable or wireless signal communication to any of the components referred to herein—e.g., to the blood pump 101—in order to control or close-loop control the blood treatment apparatus 100.

The optional pump 111 is provided to supply the second line 305 with substituate from the optional source 201, for example a bag, via an optional existing bag heating H1 with a heating bag.

Figure 2:
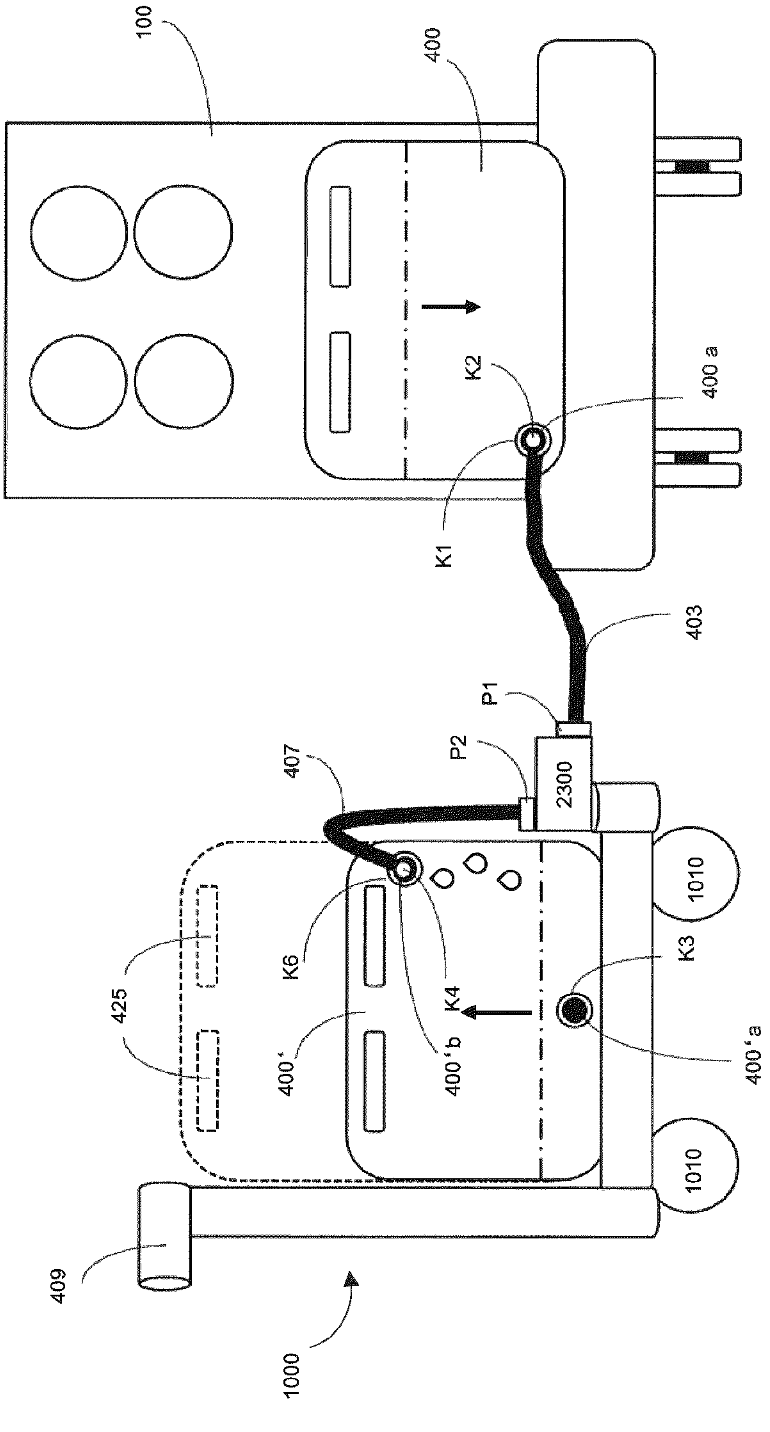
FIG. 2 shows a simplified illustration of a system with a blood treatment apparatus and a bag holder in a first embodiment.

FIG. 2 shows a simplified illustration of a system for treating a patient's blood in a first embodiment.

On the right, the second effluent bag 400 is arranged on the blood treatment apparatus 100 which usually has a capacity of 10 l by way of example. In the second effluent bag 400, effluent accumulating during an ongoing treatment can be collected.

To the left of the blood treatment apparatus 100, a bag holder 1000 is shown in FIG. 2, on or at which a first effluent bag 400' is arranged. The first effluent bag 400' may optionally include a considerably larger capacity than the second effluent bag 400 of the blood treatment apparatus 100. This is indicated by a dashed line.

Exemplary filling levels or liquid levels of the two effluent bags 400' and 400 are marked with dot-dash lines.

Figure 3:
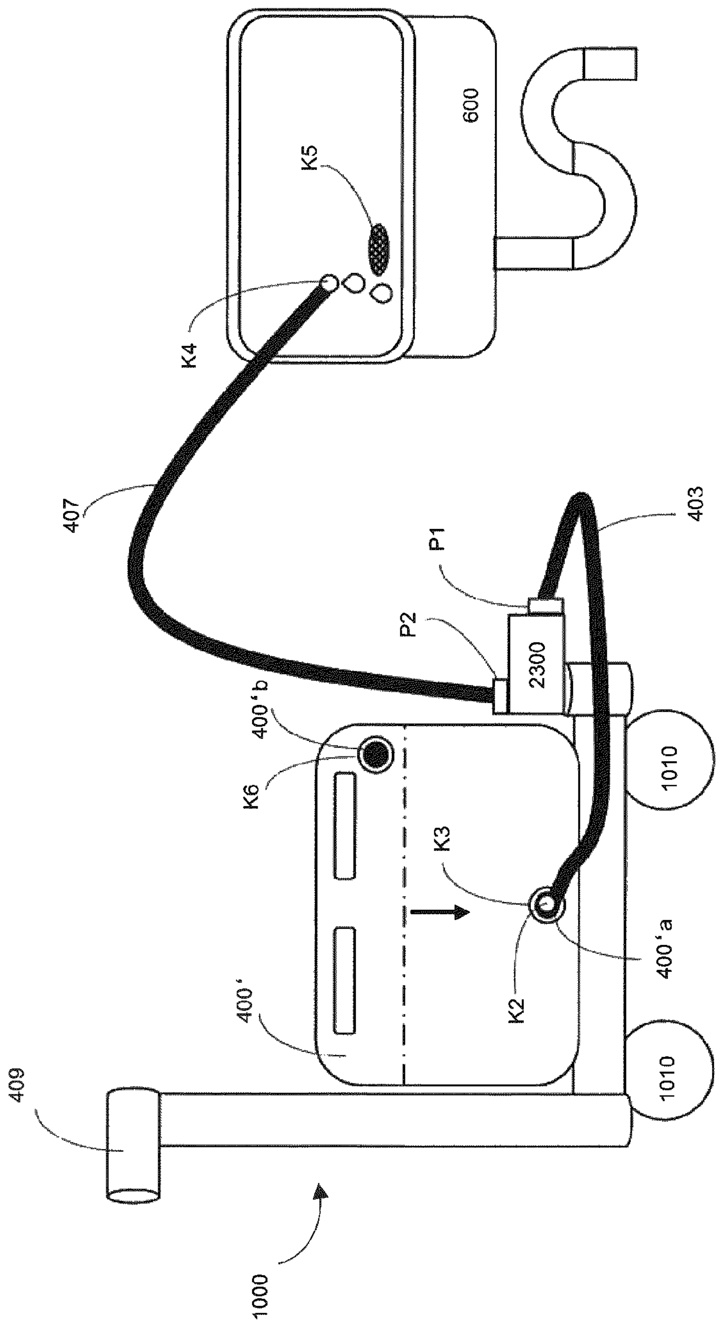
FIG. 3 shows the bag holder of the system of FIG. 1 next to a basin for emptying the first effluent bag.

The two effluent bags 400' and 400 may have at their upper end, with reference to FIGS. 2 and 3, eyelets 425 for their attachment, for example to hooks, to the blood treatment apparatus 100 or to the bag holder 1000, respectively.

In FIG. 2, a pump section 2300 with a first and a second coupling P1 or P2 can be seen on the bag holder 1000. Here, the first coupling P1 is connected to one end of an effluent outlet line 403 and the second coupling P2 is connected to one end of a basin line 407.

At the end of the effluent outlet line 403 opposite of the first coupling P1, said line optionally has a second connector K2, with which it is connected (in the procedure for emptying the second effluent bag 400 shown in FIG. 2) to the first connector K1 (see FIG. 1) of the second effluent bag 400 of the treatment apparatus 100. In this way, a fluid communication is established between the interior of the second effluent bag 400 and the interior of the effluent outlet line 403.

At its end opposite of the second coupling P2, the basin line 407 optionally has a fourth connector K4, by which it is connected to a sixth connector K6 of the first effluent bag 400'. In this way, a fluid communication is established between the interior of the basin line 407 and the interior of the first effluent bag 400'.

Thus, the interior of the second effluent bag 400 and the interior of the first effluent bag 400' are here fluidically connected via the effluent outlet line 403, the pump section 2300 and the basin line 407. Via the pump sections 2300, effluent may be pumped from the second effluent bag 400 into the first effluent bag 400'.

A pumping process is indicated in FIG. 2 by effluent drops. During the pumping process, the second effluent bag 400 now empties and the first effluent bag 400' fills to the same extent, whereby the liquid levels change according to the arrows in FIG. 2.

After the pumping process is completed, for example when the second effluent bag 400 at the blood treatment apparatus 100 has been completely emptied, or when a predetermined period of time has elapsed, the second connector K2 of the effluent outlet line 403 can be detached from the first connector K1 of the second effluent bag 400 and connected to a third connector K3 of the first effluent bag 400'. The effluent outlet opening 400*a* of the second effluent bag 400 may be closed, for example by a stopcock.

The bag holder 1000, uncoupled in this way from the second effluent bag 400 of the blood treatment apparatus 100, can now be moved by its rollers or wheels 1010 to a basin 600 (see FIG. 3), for example, it is pulled or pushed by the outlined handle 409.

If the first effluent bag 400' is received in a bowl in or at the bag holder 1000, a through-opening for the effluent outlet line 403 must be provided in the vicinity of the effluent outlet opening 400'*a*.

FIG. 3 shows the bag holder 1000 of the system from FIG. 2 next to a basin 600 when emptying the first effluent bag 400'.

After the bag holder 1000 has been positioned next to the basin 600, here a sink, the fourth connector K4 of the basin line 407 can be detached from the sixth connector K6 of the first effluent bag 400 and the basin line 407 can be positioned, for example hung, in or above the basin 600.

It is conceivable to connect the fourth connector K4 of the bowl line 407 to an optional fifth connector K5 of the basin 600, for example, in order to provide drip-proof fixing of the basin line 407 when the first effluent bag 400' is emptied. Such a fifth connector K5 is conceivable for all types of basins 600, including, for example, disposal lines within media supplies or at wallboards.

If the basin line 407 is positioned in, at or over the basin 600, the effluent may be discarded out of the first effluent bag 400' into the basin 600 by the pump section 2300 via the effluent outlet line 403 and the basin line 407.

A reverse function of the pump section 2300 is not required as the pump direction may be the same both when filling the first effluent bag 400 and when emptying it. It is therefore advantageously also possible for the pump section 2300 to have an impeller.

Figure 4:
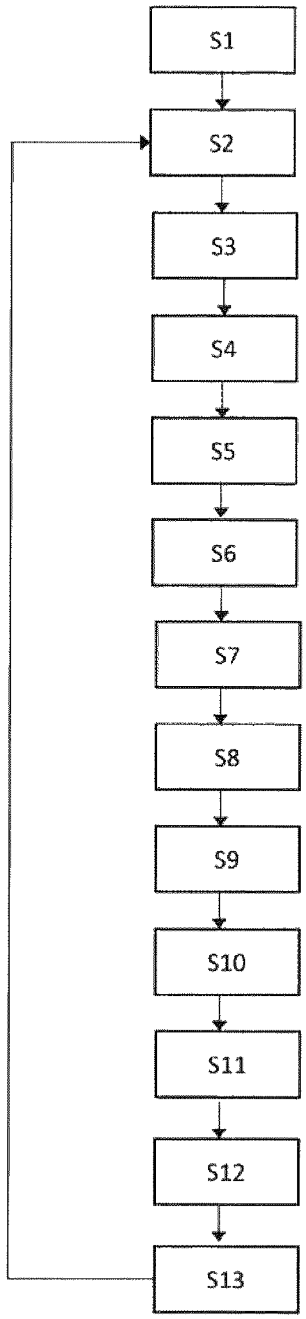
FIG. 4 shows an exemplary embodiment of the method described herein.

FIG. 4 shows an exemplary embodiment of the method described herein.

Hereby, the bag holder 1000 is in step S1, which concerns the provision thereof, in an initial position in which the second connector K2 of the effluent outlet line 403 is optionally connected to the third connector K3 of the first effluent bag 400'. The fourth K4 connector of the basin line 407 is optionally connected to the sixth connector K6 of the first effluent bag 400'.

Step S2 represents placing the bag holder 1000 near the blood treatment apparatus 100, for example by moving, pushing and/or pulling it using the rollers or the wheels 1010.

In step S3, a bag change interval is started on the blood treatment apparatus 100, optionally by disconnecting the machine-side effluent inlet line or dialysate outlet line 102 from the inlet of the second effluent bag 400, which is not shown in the figures. This optional procedure is not shown in any of the other figures.

Step S4 represents separating the second connector K2 of the effluent outlet line 403 from the third connector K3 and connecting the second connector K2 to the first connector K1 of the second effluent bag 400, which for example hangs on or at a balance scale of the blood treatment apparatus 100.

In step S5, a shut-off device is opened at or upstream of the first connector K1 and then in step S6 the effluent is pumped by the pump section 2300 from the second effluent bag 400 of the blood treatment apparatus 100 via the effluent outlet line 403 and the basin line 407 via the sixth connector K6 into the first effluent bag 400' of the bag holder 1000. The pumping may continue until the second effluent bag 400 of the blood treatment apparatus 100 is completely emptied.

After the pumping procedure in step S6, the second connector K2 of the effluent outlet line 403 is separated from the first connector K1 of the second effluent bag 400 in step S7.

In step S8, the second connector K2 of the effluent outlet line 403 is connected to the third connector K3 of the first effluent bag 400' of the bag holder 1000.

The bag holder 1000, separated from the second effluent bag 400 in this way, may now in step 9 be moved by the rollers or wheels 1010 to the vicinity of a basin 600, for example a sink or a toilet, in order to discard the effluent there. For this purpose, the optional braking device may be activated so that the bag holder 1000 stands securely.

In step S10, the fourth connector K4 of the basin line 407 is separated from the sixth connector K6 of the first effluent bag 400'.

Using the fourth connector K4 of the basin line 407, it can now in step S11 be connected to the optional fifth connector K5 of the basin 600. The fifth connector K5 may, for example, also be a disposal connector of a media supply and may be located for example in a wallboard. Alternatively, the basin line 407 can also be for example inserted or hung directly into or over the basin 600 without being fixed by the connector(s) K4 or K5.

In Step S12, the content of the first effluent bag 400' may now be pumped out by the pump section 2300 into the basin 600 via the effluent outlet line 403 and the basin line 407.

After the pumping process has been completed, the fourth connector K4 of the basin line 407 is in step S13 optionally separated again from the fifth connector K5 of the basin 600.

Subsequently, the fourth connector K4 of the outlet line 407 is connected to the sixth connector K6 of the first effluent bag 400', which brings the bag holder 1000 back to the initial position described in step S1.

The method may now be repeated starting from step S2 arbitrarily or as often as necessary, e.g., several times during a treatment session.

LIST OF REFERENCE NUMERALS

25 addition site for Heparin (optional)
29 venous blood chamber (optional)
31 ventilation or deaeration device
100 blood treatment apparatus
101 blood pump
102 dialysate outlet line, effluent inlet line
104 dialysis liquid inlet line
111 substituate pump
121 dialysis liquid pump
131 pump for dialysate or effluent in the effluent inlet line
150 control device or closed-loop control device
200 dialysis liquid source
201 substituate source, optional
300 extracorporeal blood circuit
301 first line (arterial line section)
302 (first) hose clamp
303 blood filter or dialyzer
**303*a*** dialysis liquid chamber
**303*b*** blood chamber
**303*c*** semi-permeable membrane
305 second line (venous line section)
306 (second) hose clamp
400' first effluent bag
**400'*a*** effluent outlet opening
**400'*b*** effluent inlet opening
400 second effluent bag
**400*a*** effluent outlet opening
403 effluent outlet line
407 basin line
409 handle
425 eyelets
600 basin
1000 bag holder
1010 rollers; wheels
2300 pump section
H2 bag heating with heating bag (dialysis liquid)
H1 bag heating with heating bag (substituate)
K1 first connector
K2 second connector
K3 third connector
K4 fourth connector
K5 fifth connector
K6 sixth connector
P1, P2 first or second coupling of the pump section
PS1, PS2 arterial pressure sensor (optional)
PS3 pressure sensor (optional)
PS4 pressure sensor for measuring the filtrate pressure
S1 bis S13 method steps

The invention claimed is:

1. A bag holder comprising:

one or several rollers or wheels;

a pump section comprising a liquid inlet comprising a first coupling (P1) and a liquid outlet comprising a second coupling (P2);

at least one effluent outlet line coupled to the first coupling (P1); and at least one basin line coupled to the second coupling (P2), wherein the bag holder is configured to receive a first effluent bag, which serves for receiving effluent from a second effluent bag and resulting from a blood treatment executed using a blood treatment apparatus, wherein:

the first effluent bag comprises a closable effluent outlet opening and at least one effluent inlet opening, the second effluent bag comprises an effluent outlet opening comprising a first connector (K1) of a first type, the at least one effluent outlet line comprises a second connector (K2) of the first type, the second connector (K2) configured for selective fluid communication with the first connector (K1), the first effluent bag comprises a third connector (K3) of the first type at the closable effluent outlet opening, the third connector (K3) configured for connection with the second connector (K2), and the at least one basin line comprises a fourth connector (K4) of a second type, the fourth connector (K4) configured for connection with a sixth connector (K6) of the second type, the sixth connector (K6) being located at the at least one effluent inlet opening of the first effluent bag.

2. The bag holder according to claim 1, wherein the at least one effluent inlet opening is placed higher than the closeable effluent outlet opening.

3. The bag holder according to claim 1, wherein the pump section is arranged beneath the closable effluent outlet opening in order to connect the pump section to the at least one effluent outlet line or to the at least one basin line.

4. The bag holder according to claim 1, further comprising a handle for pushing or pulling the bag holder.

5. A system for a treatment of blood of a patient, the system comprising:

a bag holder, comprising:

one or several rollers or wheels;

a pump section comprising:

a liquid inlet comprising a first coupling (P1); and a liquid outlet comprising a second coupling (P2); and at least one effluent outlet line coupled to the first coupling (P1);

at least one basin line coupled to the second coupling (P2);

a first effluent bag, comprising:

a closable effluent outlet opening; and at least one effluent inlet opening; and a blood treatment apparatus for receiving effluent resulting from the treatment of the blood of the patient using the blood treatment apparatus, the blood treatment apparatus comprising a second effluent bag comprising an effluent outlet opening comprising a first connector (K1) of a first type, wherein:

the at least one effluent outlet line comprises a second connector (K2) of the first type, the second connector (K2) configured for selective fluid communication with the first connector (K1), the first effluent bag comprises a third connector (K3) of the first type at the closable effluent outlet opening, the third connector (K3) configured for connection with the second connector (K2), the at least one basin line comprises a fourth connector (K4) of a second type, the fourth connector (K4) configured for connection with a sixth connector (K6) of the second type, the sixth connector (K6) being located at the at least one effluent inlet opening of the first effluent bag, and, the blood treatment apparatus is in fluid communication with the second effluent bag in order to bring the effluent into the second effluent bag during the treatment of the blood.

6. The system according to claim 5, wherein the blood treatment apparatus is configured as a hemodialysis apparatus, a hemofiltration apparatus, or a hemodiafiltration apparatus.

7. The system according to claim 6, wherein the blood treatment apparatus is configured as an apparatus for acute renal replacement therapy, chronic renal replacement therapy, or continuous renal replacement therapy.

8. The system according to claim 5, wherein:

the at least one effluent outlet line comprises a first end and a second end, wherein the first end of the at least one effluent outlet line is connected to the first coupling of the pump section, the second end of the at least one effluent outlet line comprises the second connector (K2) of the first type for connection with the first connector (K1) at the effluent outlet opening of the second effluent bag, and the second connector (K2) at the second end of the at least one effluent outlet line is couplable to the third connector (K3) of the first effluent bag.

9. The system according to claim 8, wherein:

the at least one basin line comprises a first end and a second end, wherein the first end of the at least one basin line is connected to the second coupling of the pump section, the second end of the at least one basin line comprises the fourth connector (K4) of the second type, and the system further comprises a basin having a fifth connector (K5) for connection with the fourth connector (K4).

10. A method of treating blood of a patient, the method comprising:

providing the system according to claim 5, wherein the second effluent bag is at least partially filled with the effluent during the treatment of the blood of the patient;

connecting the first connector (K1) of the effluent outlet opening of the second effluent bag to the at least one effluent outlet line extending from the pump section in order to guide the effluent out of the second effluent bag such that a fluid communication is established between an interior of the second effluent bag and an interior of the at least one effluent outlet line; and conveying the effluent out of the interior of the second effluent bag, wherein the effluent is sucked out of the interior of the second effluent bag by the pump section and through the at least one effluent outlet line and wherein, through the at least one basin line, the effluent is pumped with the pump section into the first effluent bag of the bag holder.

11. The method according to claim 10, further comprising:

emptying the effluent out of the first effluent bag and into a basin, wherein the emptying of the effluent comprises:

connecting the at least one effluent outlet line to the closable effluent outlet opening of the first effluent bag by connecting the second connector (K2) of the at least one effluent outlet line to the third connector (K3) of the closable effluent outlet opening;

arranging the fourth connector (K4) of the at least one basin line over the basin or in the basin; and conveying the effluent out of the first effluent bag, wherein, through the at least one effluent outlet line and by the pump section, wherein the effluent is sucked out of the first effluent bag and wherein, along the at least one basin line, the effluent is pumped into or over the basin.

12. The method according to claim 11, wherein the bag holder is moved using the one or several rollers or wheels towards the basin in order to empty the effluent out of the first effluent bag that is at least partially filled and into the basin.

13. The method according to claim 10, wherein the fourth connector is connected to a fifth connector.

* * * * *